United States Patent
Koulai

(10) Patent No.: US 10,292,873 B2
(45) Date of Patent: May 21, 2019

(54) SANITARY NAPKIN

(71) Applicant: Mezi Koulai, Carrollton, TX (US)

(72) Inventor: Mezi Koulai, Carrollton, TX (US)

( * ) Notice: Subject to any disclaimer, the term of this patent is extended or adjusted under 35 U.S.C. 154(b) by 226 days.

(21) Appl. No.: 15/211,339

(22) Filed: Jul. 15, 2016

(65) Prior Publication Data

US 2018/0014982 A1    Jan. 18, 2018

(51) Int. Cl.
*A61F 13/472* (2006.01)
*A61F 13/47* (2006.01)
*A61F 13/56* (2006.01)
*A61F 13/505* (2006.01)
*A61F 13/15* (2006.01)

(52) U.S. Cl.
CPC ...... *A61F 13/47272* (2013.01); *A61F 13/472* (2013.01); *A61F 13/505* (2013.01); *A61F 13/5616* (2013.01); *A61F 2013/16* (2013.01)

(58) Field of Classification Search
CPC .............. A61F 13/4752; A61F 13/4755; A61F 13/4756; A61F 13/476; A61F 13/47272; A61F 2013/47281
USPC .................................................. 604/385.08
See application file for complete search history.

(56) References Cited

U.S. PATENT DOCUMENTS

| | | | | |
|---|---|---|---|---|
| 3,954,107 A | * | 5/1976 | Chesky | A61F 13/47218 604/370 |
| 4,480,000 A | * | 10/1984 | Watanabe | A61F 13/51498 428/76 |
| 4,605,403 A | | 8/1986 | Tucker | |
| 4,608,047 A | * | 8/1986 | Mattingly | A61F 13/4757 604/387 |
| 4,988,344 A | * | 1/1991 | Reising | A61F 13/535 604/358 |
| 5,151,091 A | * | 9/1992 | Glaug | A61F 13/4756 604/378 |
| 5,211,641 A | * | 5/1993 | Roos | A61F 13/4752 604/385.201 |
| 5,312,386 A | | 5/1994 | Correa et al. | |
| 5,383,868 A | * | 1/1995 | Hyun | A61F 13/47227 604/385.17 |
| 5,578,025 A | * | 11/1996 | May | A61F 13/15203 604/368 |
| 5,599,337 A | * | 2/1997 | Mccoy | A61F 13/47227 604/367 |
| 5,624,423 A | * | 4/1997 | Anjur | A61F 13/47227 604/369 |

(Continued)

FOREIGN PATENT DOCUMENTS

WO    WO2005000175    1/2005

*Primary Examiner* — Susan S Su

(57) ABSTRACT

A sanitary napkin for retention of vulvar discharge includes a shell that defines an interior space. The shell is flexible and liquid impermeable. A ridge, which defines a canal, extends from the front of the shell around a perimeter of an opening. An absorbent is positioned in the interior space and the canal. A pair of fasteners is coupled singly to and extends from opposing edges of the shell. A first improvement is the liquid impermeability of the front of the shell, wherein vulvar discharge is effectively retained within the interior space of the shell. A second improvement is the ridge that is positioned on the front. The shell is sealably positionable over the vulva of the user such that vulvar discharge is directed to the opening.

13 Claims, 2 Drawing Sheets

(56) References Cited

U.S. PATENT DOCUMENTS

| | | | |
|---|---|---|---|
| 5,755,710 A * | 5/1998 | Menard | A61F 13/15585 |
| | | | 604/378 |
| 5,766,213 A * | 6/1998 | Hackman | A61F 13/4702 |
| | | | 604/385.01 |
| 6,059,763 A | 5/2000 | Brown | |
| 6,300,538 B1 * | 10/2001 | Lindquist | A61F 13/4752 |
| | | | 604/369 |
| 6,315,766 B1 | 11/2001 | Drevik | |
| D452,563 S | 12/2001 | Mok | |
| 6,764,477 B1 * | 7/2004 | Chen | A61F 13/4702 |
| | | | 604/385.14 |
| 6,852,904 B2 | 2/2005 | Sun et al. | |
| 6,863,664 B2 | 3/2005 | Wada et al. | |
| 6,939,333 B1 | 9/2005 | Franklin, Jr. | |
| 6,984,225 B2 * | 1/2006 | Raidel | A61F 13/4755 |
| | | | 604/378 |
| 9,066,837 B2 * | 6/2015 | Kim | A61F 13/4756 |
| 2003/0120233 A1 * | 6/2003 | Ohshima | A61F 13/4752 |
| | | | 604/369 |
| 2003/0139724 A1 * | 7/2003 | Ragnarson | A61F 13/47272 |
| | | | 604/385.08 |
| 2004/0236298 A1 * | 11/2004 | Coates | A61F 13/476 |
| | | | 604/385.04 |
| 2006/0069366 A1 * | 3/2006 | Cole | A61F 13/535 |
| | | | 604/378 |
| 2006/0161123 A1 * | 7/2006 | Kudo | A61F 13/84 |
| | | | 604/383 |
| 2008/0172018 A1 * | 7/2008 | Chien | A61F 13/47227 |
| | | | 604/385.04 |
| 2008/0172019 A1 * | 7/2008 | Chien | A61F 13/47218 |
| | | | 604/385.04 |
| 2009/0112173 A1 * | 4/2009 | Bissah | A61F 13/536 |
| | | | 604/378 |
| 2010/0057031 A1 * | 3/2010 | Kuroda | A61F 13/4704 |
| | | | 604/379 |
| 2010/0318056 A1 * | 12/2010 | Tucker | A61F 13/47227 |
| | | | 604/387 |
| 2010/0331804 A1 * | 12/2010 | Larsson | A61F 13/4704 |
| | | | 604/385.23 |
| 2011/0060303 A1 * | 3/2011 | Bissah | A61F 13/4756 |
| | | | 604/372 |
| 2012/0271268 A1 * | 10/2012 | Suzuki | A61F 13/15707 |
| | | | 604/385.101 |
| 2013/0035656 A1 * | 2/2013 | Moriya | A61F 13/4704 |
| | | | 604/380 |
| 2014/0066874 A1 * | 3/2014 | Hopkins | A61F 13/539 |
| | | | 604/378 |
| 2016/0213526 A1 * | 7/2016 | Taniguchi | A61F 13/476 |
| 2016/0302978 A1 * | 10/2016 | Lindstrom | A61F 13/4704 |
| 2017/0367904 A1 * | 12/2017 | Chien | A61F 13/47272 |

* cited by examiner

SANITARY NAPKIN

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIE THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to sanitary napkins and more particularly pertains to a new sanitary napkin for retention of vulvar discharge.

BRIEF SUMMARY OF THE INVENTION

An embodiment of the disclosure meets the needs presented above by generally comprising a shell that defines an interior space. The shell is flexible and liquid impermeable. A ridge, which defines a canal, extends from the front of the shell around a perimeter of an opening. An absorbent is positioned in the interior space and the canal. A pair of fasteners is coupled singly to and extends from opposing edges of the shell. A first improvement is the liquid impermeability of the front of the shell, wherein vulvar discharge is effectively retained within the interior space of the shell. A second improvement is the ridge that is positioned on the front. The shell is sealably positionable over the vulva of the user such that vulvar discharge is directed to the opening.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
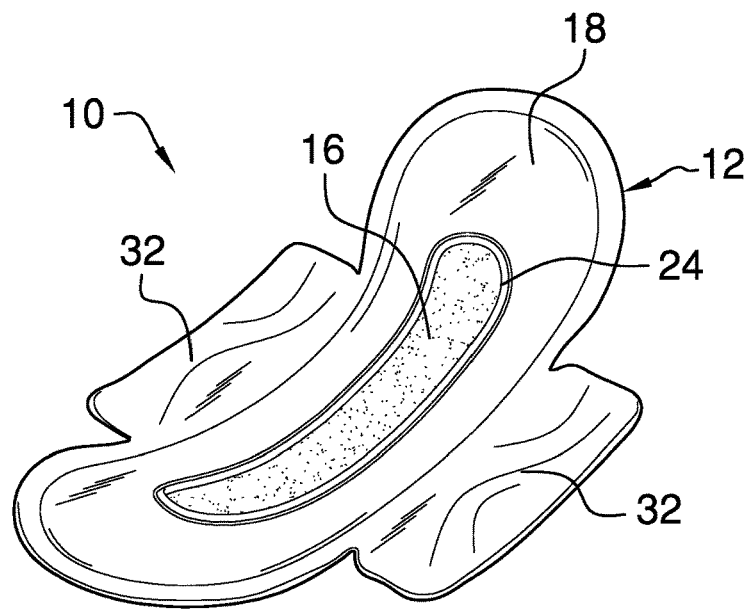
FIG. 1 is an isometric perspective view of a sanitary napkin according to an embodiment of the disclosure.
Figure 2:
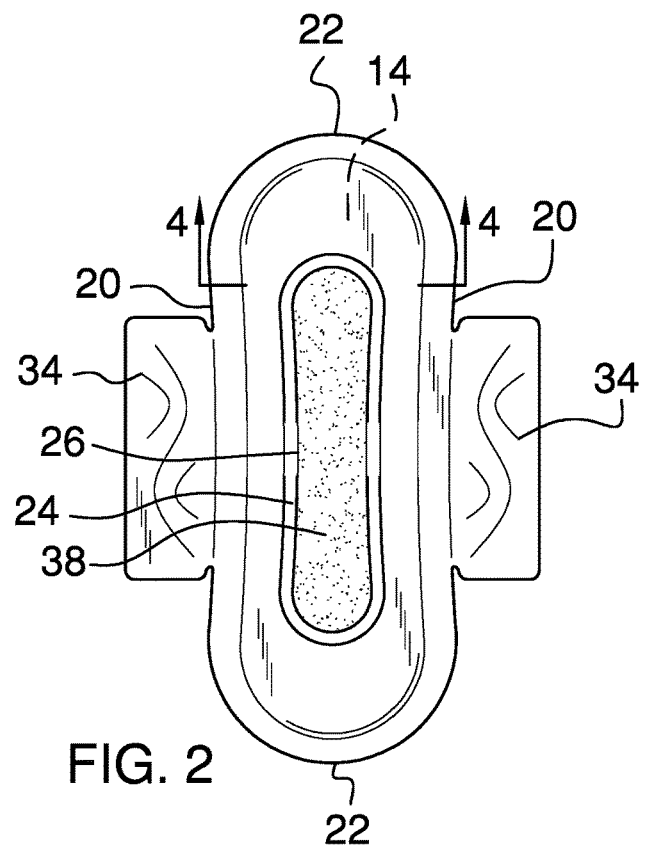
FIG. 2 is a front view of an embodiment of the disclosure.
Figure 3:
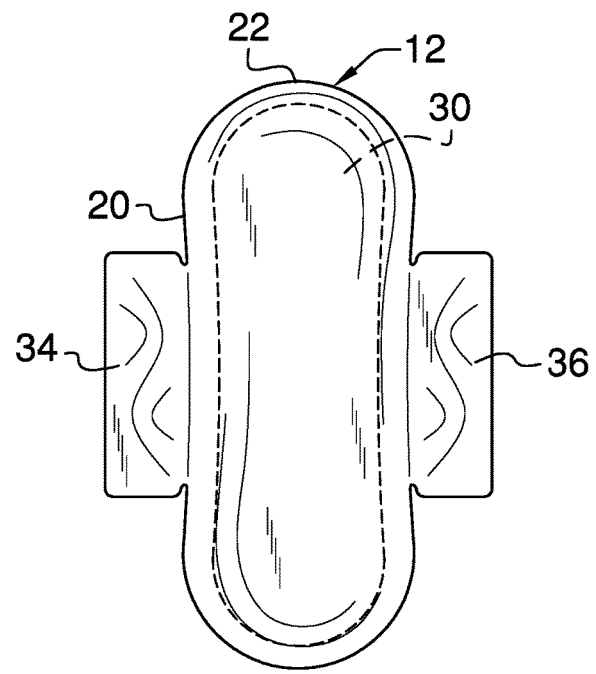
FIG. 3 is a back view of an embodiment of the disclosure.
Figure 4:
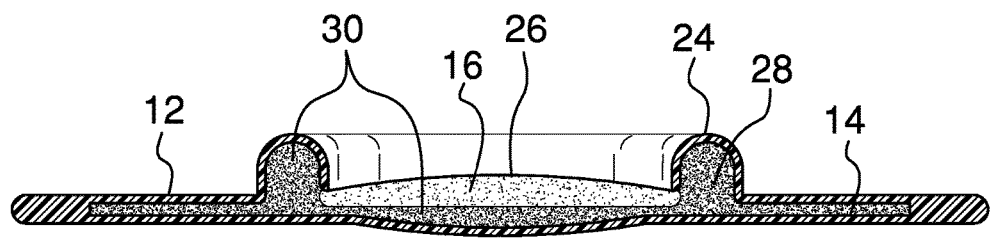
FIG. 4 is a cross-sectional view of an embodiment of the disclosure.

With reference now to the drawings, and in particular to FIGS. 1 through 4 thereof, a new sanitary napkin embodying the principles and concepts of an embodiment of the disclosure and generally designated by the reference numeral 10 will be described.

As best illustrated in FIGS. 1 through 4, the sanitary napkin 10 generally comprises a shell 12 that defines an interior space 14. The shell 12 is flexible and liquid impermeable. In one embodiment, the shell 12 comprises plastic.

An opening 16 is positioned in a front 18 of the shell 12. The opening 16 is positioned substantially equally distant from opposing edges 20 of the shell 12. The opening 16 is positioned substantially equally distant from opposing ends 22 of the shell 12. In one embodiment, the opposing ends 22 of the shell 12 are arcuate.

A ridge 24 extends from the front 18 of the shell 12 around a perimeter 26 of the opening 16. The ridge 24 defines a canal 28. The ridge 24 is positioned on the shell 12 and is configured to sealably contact the skin of the user. In one embodiment, the ridge 24 is arcuate.

An absorbent 30 is positioned in the interior space 14 and the canal 28. The absorbent 30 is configured to retain vulvar discharge that enters the opening 16 within the interior space 14. In one embodiment, the absorbent 30 is coupled to the shell 12 and the canal 28.

A pair of fasteners 32 is coupled singly to and extends from the opposing edges 20 of the shell 12. The fasteners 32 are positioned on the shell 12 and are configured to couple the shell 12 to an article of clothing with the opening 16 positioned proximate to the vulva of a user. The fasteners 32 are positioned substantially equally distant from the opposing ends 22 of the shell 12. In one embodiment, the fasteners 32 comprise tabs 34. Each tab 34 has a rear face 36 that comprises adhesive. In another embodiment, the tabs 34 are substantially rectangularly shaped.

In another embodiment, the sanitary napkin 10 comprises a cover 38 that is complimentary to the opening 16. The cover 38 is coupled to the shell 12 such that the cover 38 extends over the opening 16. The cover 38 is liquid permeable. The cover 38 is positioned over the opening 16 such that the cover 38 is positioned between the absorbent 30 and the user. In one embodiment, the cover 38 comprises perforated plastic.

In use, the fasteners 32 are configured to couple the shell 12 to an article of clothing with the opening 16 positioned proximate to the vulva of a user. A first improvement is the liquid impermeability of the front 18 of the shell 12, wherein vulvar discharge is effectively retained within the interior space 14 of the shell 12. A second improvement is the ridge 24 that is positioned on the front 18. The shell 12 is sealably positionable over the vulva of the user such that vulvar discharge is directed to the opening 16.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A sanitary napkin comprising:
    a shell defining an interior space, said shell being flexible, said shell being liquid impermeable;
    an opening positioned in a front of said shell;
    a ridge integrally extending from said front of said shell around a perimeter of said opening defining a canal within said ridge, wherein said ridge is positioned on said shell such that said ridge is configured to sealably contact the skin of the user;
    an absorbent positioned in said interior space and extending into and occupying said canal;
    a pair of fasteners coupled singly to and extending from opposing edges of said shell, wherein said fasteners are positioned on said shell such that said fasteners are configured for coupling of said shell to an article of clothing, such that said opening is positioned proximate to the vulva of a user; and
    wherein said front of said shell is liquid impermeable such that vulvar discharge is effectively retained within said interior space of said shell, and wherein is said ridge is positioned on said front such that said shell is sealably positionable over the vulva of the user such that vulvar discharge is directed to said opening.

2. The sanitary napkin of claim 1, wherein said shell comprises plastic.

3. The sanitary napkin of claim 1, wherein said opening is positioned substantially equally distant from opposing edges of said shell.

4. The sanitary napkin of claim 3, wherein said opening is positioned substantially equally distant from opposing ends of said shell.

5. The sanitary napkin of claim 4, wherein said opposing ends are arcuate.

6. The sanitary napkin of claim 1, wherein said ridge is arcuate.

7. The sanitary napkin of claim 1, said absorbent is coupled to said shell and said canal.

8. The sanitary napkin of claim 1, wherein said fasteners are positioned substantially equally distant from opposing ends of said shell.

9. The sanitary napkin of claim 1, wherein said fasteners comprise tabs having a rear face, said rear face comprising adhesive.

10. The sanitary napkin of claim 9, wherein said tabs are substantially rectangularly shaped.

11. The sanitary napkin of claim 1, further comprising a cover complimentary to said opening, said cover being coupled to said shell such that said cover extends over said opening, said cover being liquid permeable, wherein said cover is positioned over said opening such that said cover is positioned between said absorbent and the user.

12. The sanitary napkin of claim 11, wherein said cover comprises perforated plastic.

13. A sanitary napkin comprising:
    a shell defining an interior space, said shell being flexible, said shell being liquid impermeable, said shell comprising plastic;
    an opening positioned in a front of said shell, said opening being positioned substantially equally distant from opposing edges of said shell, said opening being positioned substantially equally distant from opposing ends of said shell, said opposing ends being arcuate;
    a ridge integrally extending from said front of said shell around a perimeter of said opening defining a canal within said ridge, wherein said ridge is positioned on said shell such that said ridge is configured to sealably contact the skin of the user, said ridge being arcuate;
    an absorbent positioned in said interior space and extending into and occupying said canal, said absorbent being coupled to said shell and said canal;
    a pair of fasteners coupled singly to and extending from said opposing edges of said shell, wherein said fasteners are positioned on said shell such that said fasteners are configured for coupling of said shell to an article of clothing, such that said opening is positioned proximate to the vulva of a user, said fasteners being positioned substantially equally distant from said opposing ends of said shell, said fasteners comprising tabs having a rear face, said rear face comprising adhesive, said tabs being substantially rectangularly shaped;
    a cover complimentary to said opening, said cover being coupled to said shell such that said cover extends over said opening, said cover being liquid permeable, wherein said cover is positioned over said opening such that said cover is positioned between said absorbent and the user, said cover comprising perforated plastic; and
    wherein said front of said shell is liquid impermeable such that vulvar discharge is effectively retained within said interior space of said shell, and wherein said ridge is positioned on said front such that said shell is sealably positionable over the vulva of the user such that vulvar discharge is directed to said opening.

* * * * *